(12) United States Patent
Bendall et al.

(10) Patent No.: US 7,812,968 B2
(45) Date of Patent: Oct. 12, 2010

(54) FRINGE PROJECTION SYSTEM AND METHOD FOR A PROBE USING A COHERENT FIBER BUNDLE

(75) Inventors: Clark Alexander Bendall, Syracuse, NY (US); Kevin George Harding, Niskayuna, NY (US); Guiju Song, Shanghai (CN); Li Tao, Shanghai (CN); Ming Jia, Shanghai (CN); Xinjun Wan, Shanghai (CN)

(73) Assignee: GE Inspection Technologies, LP, Lewistown, PA (US)

( * ) Notice: Subject to any disclaimer, the term of this patent is extended or adjusted under 35 U.S.C. 154(b) by 412 days.

(21) Appl. No.: 12/042,740

(22) Filed: Mar. 5, 2008

(65) Prior Publication Data

US 2009/0225320 A1    Sep. 10, 2009

(51) Int. Cl.
*G01B 9/02* (2006.01)
*G01B 11/02* (2006.01)

(52) U.S. Cl. .................. 356/521; 356/479; 356/511
(58) Field of Classification Search .......... 356/479, 356/497, 511, 521
See application file for complete search history.

(56) References Cited

U.S. PATENT DOCUMENTS

| | | | |
|---|---|---|---|
| 5,069,548 A | | 12/1991 | Boehnlein |
| 5,175,601 A | * | 12/1992 | Fitts ............................ 356/604 |
| 5,289,264 A | | 2/1994 | Steinbichler |
| 5,302,999 A | * | 4/1994 | Oshida et al. ................... 355/1 |
| 5,434,669 A | * | 7/1995 | Tabata et al. ................ 356/477 |
| 5,581,352 A | * | 12/1996 | Zeien .......................... 356/604 |
| 5,810,719 A | * | 9/1998 | Toida .......................... 600/160 |
| 5,823,942 A | * | 10/1998 | Toida .......................... 600/160 |
| 6,011,624 A | * | 1/2000 | de Groot ...................... 356/511 |
| 6,088,105 A | | 7/2000 | Link |
| 7,170,677 B1 | | 1/2007 | Bendall et al. |
| 7,388,679 B2 | * | 6/2008 | Yoshino et al. ............. 356/603 |
| 7,551,293 B2 | * | 6/2009 | Yelin et al. .................. 356/497 |
| 7,570,370 B2 | * | 8/2009 | Steinbichler et al. ........ 356/603 |
| 2005/0046872 A1 | | 3/2005 | Hu et al. |
| 2007/0109558 A1 | | 5/2007 | Harding et al. |
| 2009/0225320 A1 | * | 9/2009 | Bendall et al. .............. 356/447 |

(Continued)

OTHER PUBLICATIONS

U.S. Appl. No. 12/042,800, filed Mar. 5, 2008, Clark Alexander Bendall et al.

(Continued)

*Primary Examiner*—Patrick J Connolly
(74) *Attorney, Agent, or Firm*—Global Patent Operation; Mark A. Conklin

(57) ABSTRACT

A probe is presented that includes a light source, a coherent fiber bundle, and a pattern selector. The pattern selector is disposed between the light source and the proximal end of the coherent fiber bundle. The pattern selector includes at least one patterned zone through which light from the light source passes to project at least one fringe set onto a surface. Each of the at least one fringe sets has a structured-light pattern. The probe further includes an imager for obtaining at least one image of the surface and a processing unit that is configured to perform phase-shift analysis on the at least one image. A method for projecting a plurality of fringe sets suitable for phase-shift analysis on a surface using a probe is presented.

20 Claims, 5 Drawing Sheets

U.S. PATENT DOCUMENTS

2009/0225321 A1* 9/2009 Bendall et al. ............... 356/447
2009/0225329 A1* 9/2009 Bendall et al. ............... 356/610
2009/0225333 A1* 9/2009 Bendall et al. ............... 356/626

OTHER PUBLICATIONS

U.S. Appl. No. 12/042,821, filed Mar. 5, 2008, Clark Alexander Bendall et al.

Leonard H. Bieman, Kevin G. Harding, and Albert Boehnlein, "Absolute Measurement using Field Shifted Moire," reprinted from "Optics, Illumination, and Image Sensing for Machine Vision VI," Nov. 14-15, 1991, vol. 1614.

Kevin Harding, "Latets Optical Methods for Industrial Dimensional Metrology," SPIE Publications, Sep. 2005.

Kevin Harding and Shu-Guo Gordon Tang, "Machine Vision Method for Small Feature Measurements," SPIE Publications, Nov. 2004.

Albert Boehnlein and Kevin Harding, "Field Shift Moire, a New Technique for Absolute Range Measurement," reprinted from "Fringe Pattern Analysis," Aug. 8-9, 1989, vol. 1163.

* cited by examiner

FRINGE PROJECTION SYSTEM AND METHOD FOR A PROBE USING A COHERENT FIBER BUNDLE

BACKGROUND OF THE INVENTION

1. Field of the Invention

The subject matter described herein relates generally to borescopes and endoscopes, and more particularly, to a borescope/endoscope which provides 3D surface mapping and dimensional measurement.

2. Related Art

Borescopes and endoscopes are typically used for inspection inside a remote cavity. Most borescopes/endoscopes, referred to herein as probes, employ an external light source coupled to fiber optic bundles in the probe to provide illumination of a remote object or surface at the distal end. When the object is illuminated, an internal image is formed by a lens system on an image sensor, and the image is relayed to a connected display, such as a video screen. The image sensor may be located at the proximal end of the probe, as with an optical rigid borescope or fiberscope, or at the distal end as with a video borescope or endoscope. Such systems are often used to inspect in inaccessible locations for damage or wear or to verify that parts have been properly manufactured or assembled. Among other things, it is desirable to obtain dimensional measurements to verify that damage or wear does not exceed an operational limit or that a manufactured part or assembly meets its specifications. It may also be desirable to produce a 3D model or surface map for comparison to a reference, 3D viewing, reverse engineering, or detailed surface analysis.

The image shown on the connected display varies in magnification and apparent size depending upon the distance between the object and the distal end of the probe carrying the lens system and image sensor. This leads to difficulties in directly determining dimensional measurements, especially in three spatial dimensions.

There are a number of known approaches for providing 3D data through a probe including splitting the view to gain a stereo image (stereo viewing), projecting a coarse pattern of dots onto the remote object, or using a single line to obtain a single image profile. Stereo methods can be used to create a 3D view, but can only provide information where two points on the image can be correlated. This can be problematic when little surface detail exists. The correlation process can also require significant processing, so producing a full 3D surface map can be time consuming. It is more typical to only correlate a small number of points needed for basic measurements. Projecting a course pattern of dots permits measurement to be obtained at the points of the dots. However, the areas between the dots are left to be interpolated, so any surface variations between them are lost. Finally, a single line profile provides useful information along that single profile, but proper positioning of the single line on the object of interest can be difficult, and measurements that require non co-linear points, such as point to line or area measurements, are subject to error if the surface is not flat or the view is not perpendicular to the surface. The scanning of a single profile line that is often employed in commercial systems to build a 3D surface map is generally not practical in a small probe due to size constraints.

Other limitations also exist regarding the approaches discussed above. For example, a large computing capacity is often required to implement the solutions, and highly skilled technicians are needed to operate the equipment. In addition, the above approaches may not be appropriate when a dense 3D full surface map or full-field object measurement is desired. Without the full-field data, imperfections on a surface or object may be missed entirely. Thus, it is desirable to provide a probe that offers full-field surface mapping.

Full-field object data can be obtained through phase-shifting. Phase-shifting is an analysis technique used for non-contact optical metrology applications. Phase-shifting typically involves projecting one or more sets of parallel lines that cross the field of view (FOV) of a camera. As the object distance changes, the parallel lines, or fringe sets, shift across the FOV. Which line is which, or absolute phase, must be determined in order to make accurate measurements and obtain an accurate surface map. The absolute phase at a given point in the image is defined as the total phase difference ($2\pi$ times the number of line periods) between a reference point in the projected line pattern and the given point. The reference point can be arbitrarily defined.

There are a number of known approaches to decipher which line is which and determine absolute phase. Some approaches include employing multiple fringe sets with physical horizontal offsets resulting in a relative phase that changes with distance or using multiple fringe sets with physical axial offsets to change the period with distance. Most techniques use additional projections. For example, to assist in determining the absolute phase an extra line may be projected to give a starting reference point.

The determined absolute phase combined with the fringe set position in the FOV are used to determine absolute object distance.

Phase-shifting methods have not been practical for use in devices such as borescopes and endoscopes. The equipment required to project suitable line patterns for phase-shifting methods usually include a projector, scanner, piezo mirror, or similar item. Among other things, the size limitations of probes make the use of typical equipment mechanically challenging.

Thus, it is desirable to provide a practical mechanical configuration of a probe that is able to perform measurements and 3D surface mapping based on phase-shift analysis.

BRIEF DESCRIPTION OF THE INVENTION

In accordance with an embodiment of the present invention, a probe comprises a light source, a coherent fiber bundle, and a pattern selector. The pattern selector is disposed between the light source and the proximal end of the coherent fiber bundle. The pattern selector comprises at least one patterned zone through which light from the light source passes to project at least one fringe set onto a surface. Each of the at least one fringe sets comprises a structured-light pattern. The probe further comprises an imager for obtaining at least one image of the surface and a processing unit that is configured to perform phase-shift analysis on the at least one image.

In another embodiment of the invention, a method for projecting a plurality of fringe sets suitable for phase-shift analysis on a surface using a probe is provided. The method comprises disposing a pattern selector between a light source and the proximal end of a coherent fiber bundle, the pattern selector comprising at least one patterned zone. The method further comprises passing light from the light source through the coherent fiber bundle at the at least one patterned zone to project structured-light patterns onto the surface. The structured-light patterns are projected such that the structured-light patterns exhibit a phase-shift relative to one another, the phase-shift being compatible with phase-shift analysis.

BRIEF DESCRIPTION OF THE DRAWINGS

The following detailed description is made with reference to the accompanying drawings, in which.

DETAILED DESCRIPTION OF THE PREFERRED EMBODIMENT

Figure 1:
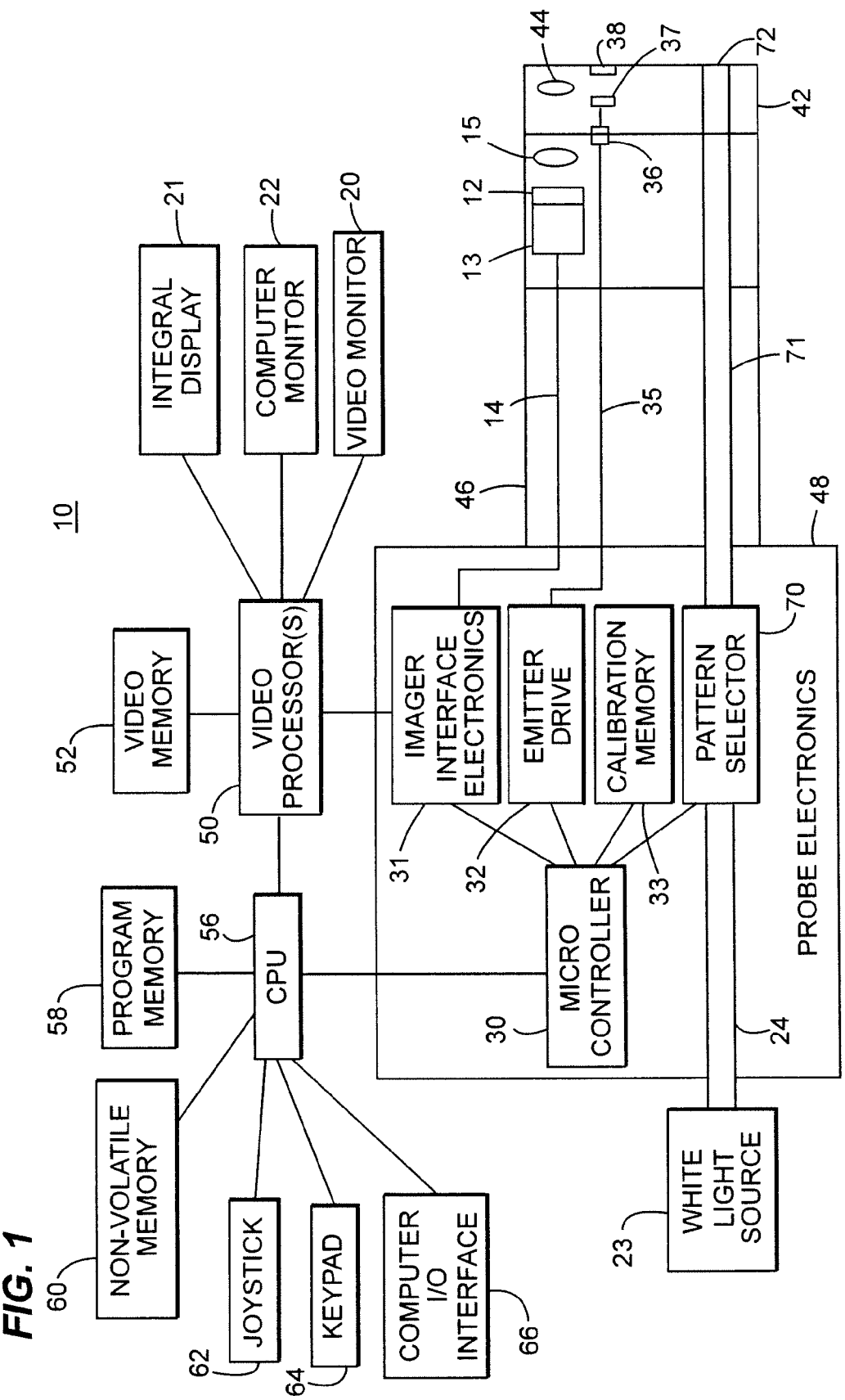
FIG. 1 is a schematic diagram of a borescope/endoscope system in accordance with one embodiment of the present invention.

Illustrated in FIG. 1, a borescope/endoscope system 10 according to an embodiment of the invention is shown. A detachable distal tip 42 contains viewing optics 44 which are used in combination with probe optics 15 to guide and focus light received from the surface or object (not shown) onto imager 12. The viewing optics may optionally include relay optics such as a lens or fiber optic system to remote the camera head away from the distal tip.

Imager 12 is included in elongated portion 46 that is typically flexible. Imager 12 may comprise, for example, a two-dimensional array of light-sensitive pixels that outputs a video signal in response to the light level sensed at each pixel. Imager 12 may comprise a charge-coupled device (CCD), complementary metal-oxide-semiconductor (CMOS) image sensor, or other devices of similar function. The video signal is buffered by electronics 13 and transferred to imager interface electronics 31 via signal line 14. Imager interface electronics 31 may include, for example, power supplies, a timing generator for generating imager clock signals, an analog front end for digitizing the imager video output signal, and a digital signal processor for processing the digitized imager video data into a more useful format for video processor 50.

Video processor 50 performs various functions not limited to image capture, image enhancement, graphical overly merging, and video format conversion and stores information relating to those functions in video memory 52. Video processor 50 may comprise field-programmable gate array (FPGA), digital signal processor (DSP), or other processing elements and provides information to and receives information from central processing unit (CPU) 56. The provided and received information may relate to commands, status information, video, still images, and/or graphical overlays. Video processor 50 also outputs signals to various monitors such as computer monitor 22, video monitor 20, and integral display 21. Video processor 50 and/or CPU 56 are used to obtain at least one digital image of the surface as sensed by imager 12.

When connected, each of computer monitor 22, video monitor 20, and/or integral display 21 typically display images of the object or surface under inspection, menus, cursors, and measurement results. Computer monitor 22 is typically an external computer type monitor. Similarly, video monitor 20 typically includes an external video monitor. Integral display 21 is integrated and built into system 10 and typically comprises a liquid crystal display (LCD).

CPU 56 preferably uses both program memory 58 and non-volatile memory 60, which may include removable storage devices. CPU 56 may also use volatile memory such as RAM for program execution and temporary storage. A keypad 64 and joystick 62 convey user input to CPU 56 for such functions as menu selection, cursor movement, slider adjustment, and articulation control. Computer I/O interface 66 provides various computer interfaces to CPU 56 such as USB, Firewire, Ethernet, audio I/O, and wireless transceivers. Additional user I/O devices such as a keyboard or mouse may be connected to computer I/O interface 66 to provide user control. CPU 56 generates graphical overlay data for display, provides recall functions and system control, is configured to perform phase-shift analysis and measurement processing, and provides image, video, and audio storage.

System 10 further comprises contacts 36 that electrically couple insertion tube 46 to detachable tip 42. Contacts 36 may be spring loaded and also provide electrical power from drive conductor 35 to emitter module 37. Drive conductor 35 carries power from emitter drive 32 to emitter module 37. Drive conductor 35 comprises one or more wires and may be incorporated with signal line 14 in a common outer jacket (not shown). Drive conductor 35 may also share conductors with signal line 14 and/or utilize the insertion tube 46 structure for carrying current. Emitter drive 32 includes, for example, an adjustable current source with a variable on time to compensate for light emitters with differing power capabilities and efficiencies.

The at least one emitter module 37 on detachable tip 42 comprises at least one light emitting element and optionally other electronics for control/sequencing of emitters, sensing temperature, and storage/retrieval of calibration data. Light from the at least one light emitting element on detachable tip 42 is passed through at least one intensity modulating element 38 to alter the distribution of light and may be used to create/project at least one calibrating light pattern on the surface. The calibrating light pattern may include, but is not limited to, angled lines, a single line, a plurality of lines, a dot, a plurality of dots, and a plurality of parallel light and dark lines.

Distal tip 42 comprising the at least one emitter module 37 may be fixedly attached to insertion tube 46 or detachable from insertion tube 46 allowing the at least one emitting module 37 and intensity modulating element 38 to be detachable from the probe. Alternatively, the at least one emitter module 37 could be fixedly attached to insertion tube 46 while intensity modulating element 38 is disposed on detachable tip 42.

Light source 23 is typically a white light source, but may comprise any appropriate light source for a probe such as a mercury or metal halide arc lamp, halogen lamp, laser/phosphor system, fiber coupled laser, or LED based light source that is proximally located. When light source 23 is not directly coupled to pattern selector 70, source fiber bundle 24 is included in system 10. Source fiber bundle 24 is disposed between light source 23 and pattern selector 70. Source fiber bundle 24 comprises a non-coherent or semi-coherent fiber optic bundle. In an embodiment of the invention, source fiber bundle 24 comprises a non-coherent inner bundle within a larger non-coherent bundle. This configuration keeps the high intensity light from light source 23 within in the inner bundle thus allowing light to pass through larger secondary bundles while still allowing a significant amount of light to pass through smaller secondary fiber bundles.

Pattern selector 70 typically includes an optically-transmissive element 100 (FIG. 2) having at least one clear zone 110 and at least one patterned zone 120. An additional zone may be included on element 100 for generating a calibrating light pattern. The calibrating light pattern may include, but is not limited to, angled lines, a single line, a plurality of lines, a dot, a plurality of dots, and a plurality of parallel light and dark lines. Light from source fiber bundle 24 passes through pattern selector 70. Pattern selector 70 is disposed between light source 23 and the proximal end of coherent fiber bundle 71 and pattern imaging optics 72 are disposed at the distal end of coherent fiber bundle 71. Therefore, light that passes through pattern selector 70 passes through coherent fiber bundle 71 to pattern imaging optics 72, which image light onto the viewed object. Pattern imaging optics 72 may comprise a conventional lens system, gradient index (GRIN) lens, or any lens system with high efficiency, low distortion, and good focus over a large working range.

The previously discussed imager interface electronics 31, emitter drive 32, and pattern selector 70 are included in the probe electronics 48. Probe electronics 48 may be physically separated from a main control unit or CPU 56 to provide more local control over probe-related operations. Probe electronics 48 further comprise calibration memory 33. Calibration memory 33 stores information relating to the optical system of detachable tip 42 and/or insertion tube 46 such as magnification data, optical distortion data, and pattern projection geometry data.

Microcontroller 30, also included in probe electronics 48, communicates with imager interface electronics 31 to determine and set gain and exposure settings, controls emitter drive 32 circuitry, stores and reads calibration data from the calibration memory 33, controls pattern selector 70, and communicates with CPU 56.

The accuracy of a system employing structured-light projection and phase-shift analysis is largely determined by its baseline spacing. The baseline spacing is the distance between the projection origin and the camera FOV origin. In this embodiment, the baseline spacing is the spacing between pattern imaging optics 72 and viewing optics 44. Detachable distal tip 42 comprises at least one lens of viewing optics 44 and pattern imaging optics 72. The greater the distance between the pattern imaging optics 72 and viewing optics 44, the higher the measurement resolution. Therefore, in order to increase measurement resolution, when the lenses of both viewing optics 44 and pattern imaging optics 72 are disposed detachable distal tip 42, viewing optics 44 are disposed on one side of detachable distal tip 42 while pattern imaging optics 72 are disposed on the other side of detachable distal tip 42.

In addition, viewing optics 44 and pattern imaging optics 72 may comprise a prism (not shown). The viewing optics 44 prism and the pattern imaging optics 72 prism may be disposed in a detachable tip adapter (not shown) of detachable distal tip 42. In some applications, it is desirable to obtain a view in a direction perpendicular to the probe axis, referred to as a side view. To obtain such a view, detachable tip 42 may comprise a side-view prism (not shown) through which the plurality of fringe sets reflected from the surface pass through viewing optics 44 to reach the imager 12.

Figure 2:
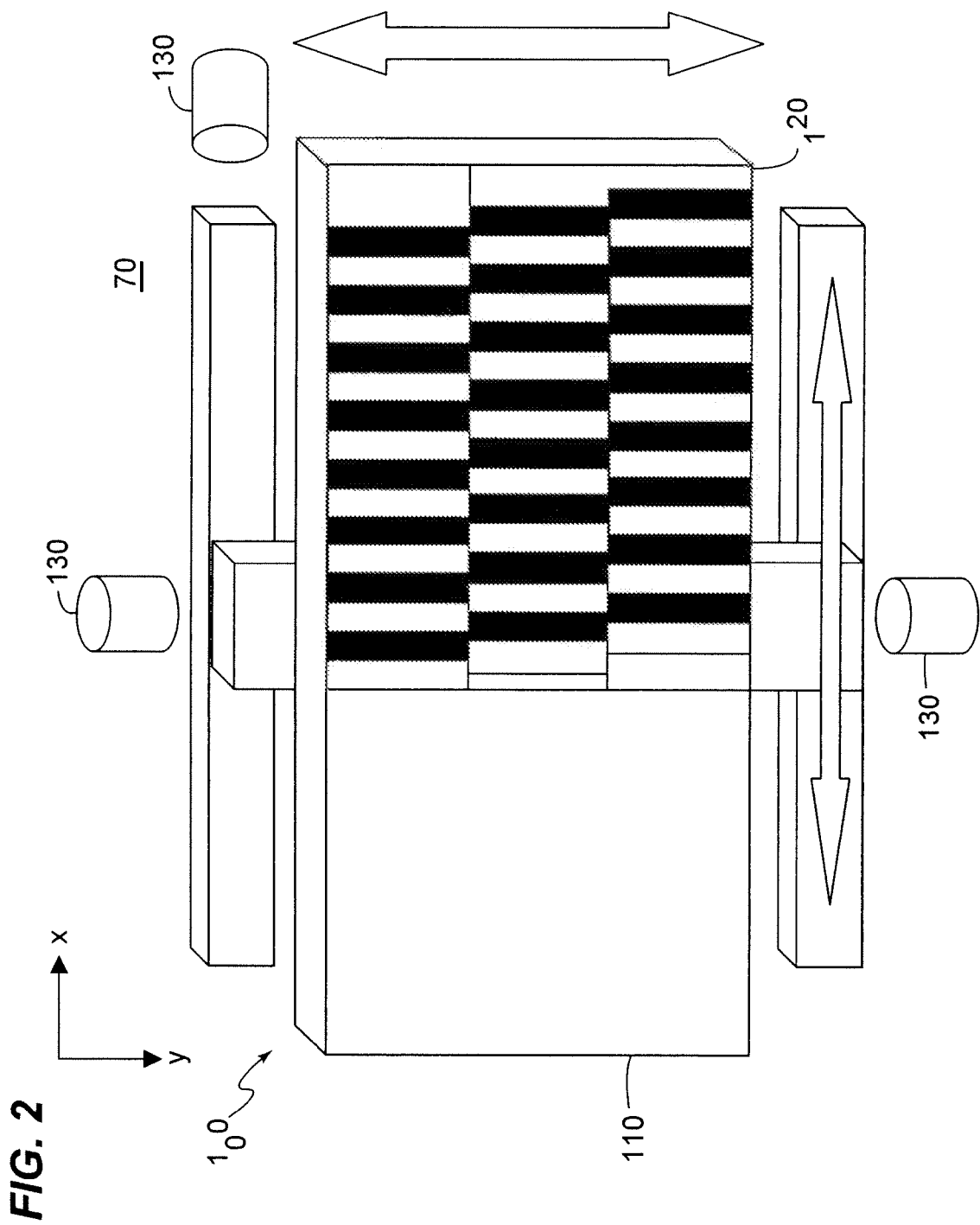
FIG. 2 is a perspective view of an exemplary pattern selector comprising an optically-transmissive element.

Referring now to FIG. 2, an exemplary embodiment of pattern selector 70 is shown. Optically-transmissive element 100 of pattern selector 70 comprises at least one clear zone 110 and at least one patterned zone 120 wherein optically-transmissive element 100 is translated between the zones in order to position either the at least one clear zone 110 or the at least one patterned zone 120 at the proximal end of coherent fiber bundle 71. In the case of FIG. 2, optically-transmissive element 100 is horizontally moveable between the at least one clear zone 110 and the at least one patterned zone 120. In an alternative embodiment, optically-transmissive element 100 is vertically moveable between the at least one clear zone 100 and the at least one patterned zone 120. In yet another alternative embodiment, optically-transmissive element 100 comprises a circular or doughnut shaped substrate on which clear zone 100 and patterned zone 120 are disposed. At least one translation element 130 such as a motor, piezo translator, or solenoid may be used to position a selected zone between source fiber bundle 24 and coherent fiber bundle 71 using linear or rotational movement.

Figure 3:
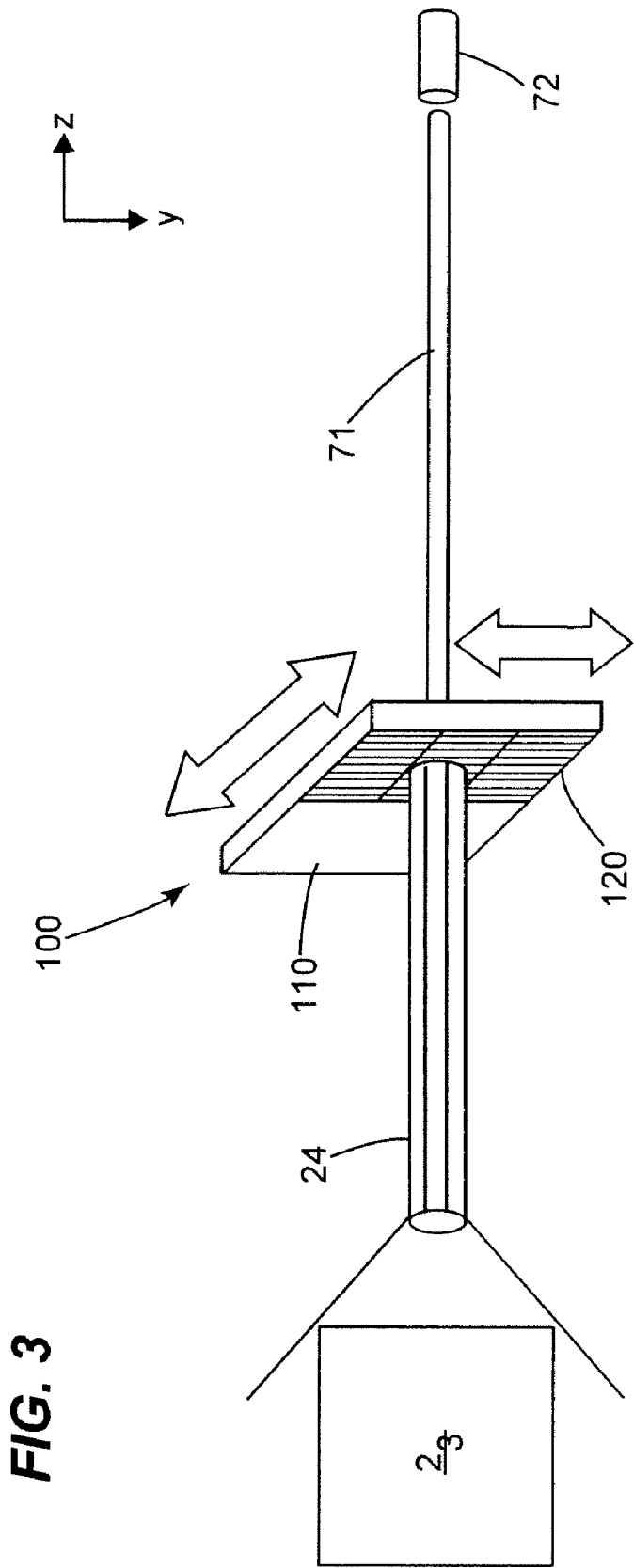
FIG. 3 is a perspective view of an exemplary configuration of the system including an optically-transmissive element.

FIG. 3 illustrates an exemplary configuration of the system including pattern selector 70 (not shown) comprising optically-transmissive element 100. Clear zone 110 passes as much light as possible from source fiber bundle 24 to coherent fiber bundle 71. Patterned zone 120 alters the distribution of light from the source fiber bundle 24 to coherent fiber bundle 71. Light from the source fiber bundle 24 passes through patterned zone 120 to form at least one structured-light pattern suitable for phase-shift analysis on the proximal end of coherent fiber bundle 71. In another embodiment, light source 23 is directly coupled to coherent fiber bundle 71 through pattern selector 70. In yet another embodiment, focusing optics are included to focus a pattern on optically-transmissive element 100 onto the proximal end of coherent fiber bundle 71.

Optically-transmissive element 100 may comprise a clear substrate, such as glass, onto which an opaque material, such as chrome, has been deposited to form the described patterns. Alternatively, optically-transmissive element 100 may comprise an opaque material, such as a thin piece of metal, in which the described patterns are formed by removing material. Clear zone 110 may comprise an optically transparent portion of a clear substrate. Clear zone 110 may also comprise a simple air gap, which may be arbitrarily small, to allow direct coupling of light from light source 23 or source fiber bundle 24 to coherent fiber bundle 71 without passing through any solid material.

Coherent fiber bundle 71 comprises optical fibers arranged in the same order at both the proximal and distal end of the fiber bundle such that a pattern or image input at one end emerges in tact at the other end. Therefore, the at least one structured-light pattern, discussed above, input at the proximal end of coherent fiber bundle 71 emerges from the distal end of coherent fiber bundle 71 to pass through pattern imaging optics 72. When patterned zone 120 is selected, pattern imaging optics 72 images the at least one structured-light pattern from the distal end of coherent fiber bundle 71 onto the viewed object. However, when clear zone 110 is selected, pattern imaging optics 72 images as much light as possible from coherent fiber bundle 71 onto the viewed object.

The probe operates in inspection mode and measurement mode. During regular inspection, or inspection mode, the at least one clear zone 110 is disposed between light source 23 and the proximal end of coherent fiber bundle 71, and as much light as possible is projected onto the viewed object. During measurement pattern projection, or measurement mode, at least one fringe set, discussed below, is projected onto the surface. During measurement mode, patterned zone 120 is disposed between light source 23 and the proximal end of coherent fiber bundle 71, and at least one image comprising a structured-light pattern on the surface is captured. Phase-shift analysis may then be performed on the at least one image.

Mentioned above, at least one structured-light pattern is created on the surface by passing light through patterned zone 120, which alters the distribution of light. In an embodiment of the present invention, the patterned zone comprises a plurality of line gratings. The structured-light pattern preferably comprises parallel light and dark lines comprising sinusoidal intensity profiles. Line patterns having square, trapezoidal, triangular, or other profiles may be projected on the surface as well when used with appropriate phase-shift analysis to determine phase of the pattern. The pattern may also comprise other than straight, parallel lines. For example, curved lines, wavy lines, zigzagging lines, or other such patterns may be used with appropriate analysis.

Figure 4:
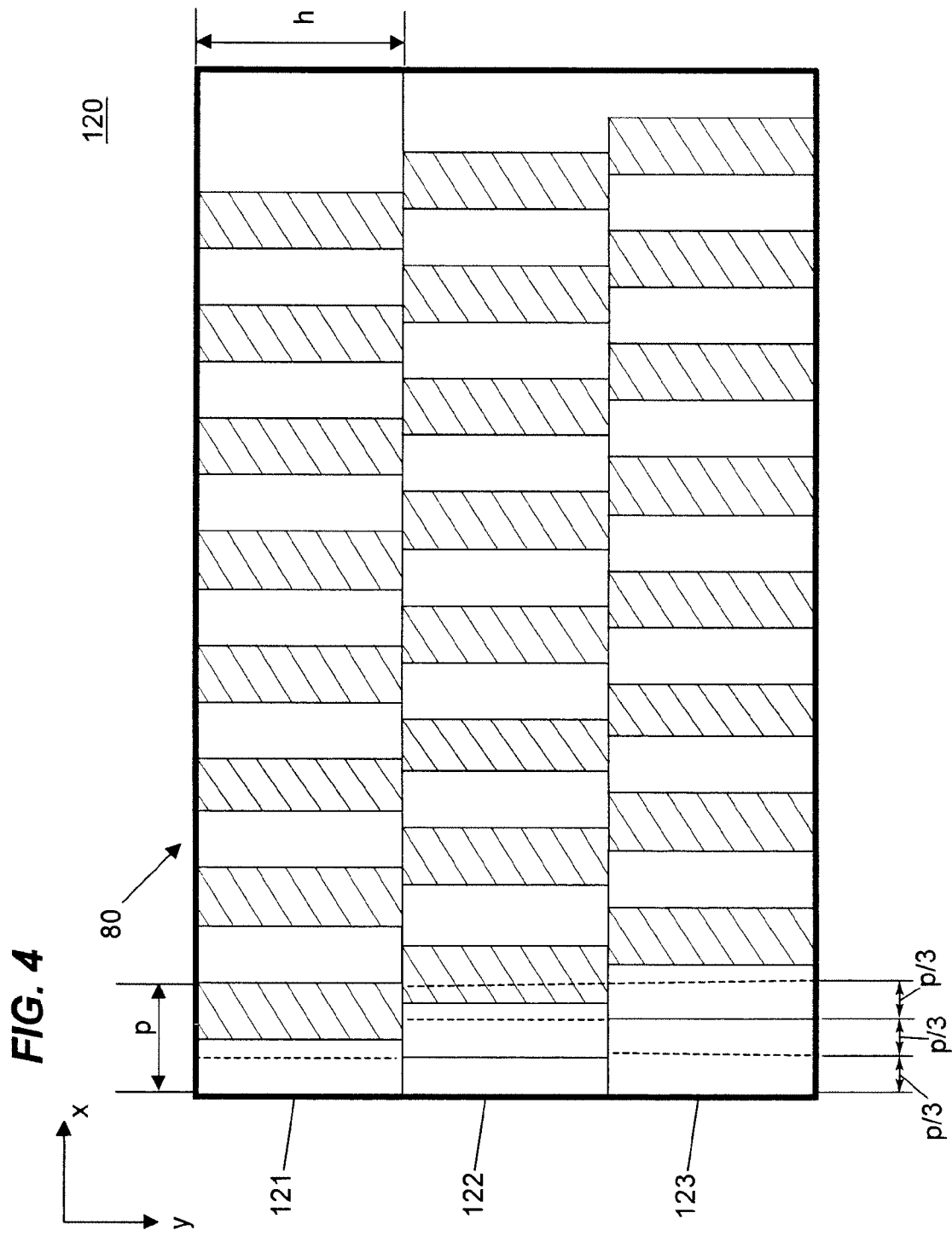
FIG. 4 is an exploded view of a patterned zone of the pattern selector shown in FIG. 2 in accordance with one embodiment of the present invention.

When patterned zone 120 is disposed between light source 23 and the proximal end of coherent fiber bundle 71, light from light source 23 passes through patterned zone 120 to project at least one fringe set onto the surface or object, each of the at least one fringe sets comprising a structured-light pattern. FIG. 4 is an exploded view of the at least one patterned zone 120 shown in FIG. 2. For illustrative purposes, the solid-colored elements of patterned zone 120 in FIG. 2 are instead shaded with diagonal lines in FIG. 4 in order to better illustrate the spatial offset or displacement between each similar intensity-modulating element 80.

Patterned zone 120 comprises a plurality of similar intensity-modulating elements 80. In an embodiment of the present invention, the plurality of similar intensity-modulating elements are vertically stacked on top of one another and the plurality of similar intensity-modulating elements 80 comprise a line grating. In a preferred embodiment, the plurality of similar intensity-modulating elements 80 comprise three similar intensity-modulating elements 121, 122, 123.

The at least one patterned zone 120 comprises a plurality of similar intensity modulating elements 80 such that when light passes through each of the plurality of similar intensity-modulating elements 80, a fringe set comprising a structured-light pattern is projected onto the surface or object. Light from light source 23 is passed through the plurality of similar intensity-modulating elements 80, disposed at the proximal end of coherent fiber bundle 71, to pattern imaging optics 72, disposed on the distal end of coherent fiber bundle, to image the plurality of fringe sets onto the surface.

The plurality of similar intensity-modulating elements 80 are positioned on patterned zone 120 such that the structured-light pattern projected when light passes through one of the plurality of similar intensity-modulating elements 80 exhibits a spatial or phase-shift relative to the structured-light pattern projected when light passes through the others of the plurality of similar intensity-modulating elements 80. In other words, the structured-light pattern of one fringe set exhibits a phase-shift relative to the structured-light patterns of other fringe sets. The spatial or phase-shift of the fringe sets are compatible with phase-shift analysis.

In an embodiment of the invention, the plurality of similar intensity-modulating elements 80 comprise a line grating having a grating period p. In FIG. 4, the plurality of similar intensity-modulating elements are positioned such that the structured-light pattern of one projected fringe set exhibits a phase-shift of ⅓ the projected line period relative to the structured-light pattern of adjacent projected fringe sets. Each light and dark line pair represents a phase range of 360° or 2π radians, so the phase-shift equates to a phase-shift of 120° or 2π/3 radians.

Again, FIG. 4 illustrates an exemplary case when the line grating of similar intensity-modulating elements 80 has a grating period p. The plurality of similar intensity-modulating elements 80 are vertically stacked such that each of the plurality of similar intensity-modulating elements is displaced from the similar intensity-modulating element directly above it by ⅓ period in the horizontal direction. Seen in FIG. 4, the vertically stacked similar intensity-modulating elements 121, 122, 123 are displaced on patterned zone 120 by ⅓ period in the x direction. In the case of FIG. 4, the plurality of similar intensity-modulating elements 80 comprise a repeating pattern with a grating period p and are stacked in a direction A such that one of the plurality of similar intensity-modulating elements is displaced from an adjacent similar intensity-modulating element by ⅓ period in the direction perpendicular to direction A.

Generally speaking, the plurality of similar intensity-modulating elements 80 comprise a repeating pattern with a grating period p and are stacked in a direction A such that one of the plurality of similar intensity-modulating elements is displaced from an adjacent similar intensity-modulating element by n/3 times the period in the direction perpendicular to direction A, where n is an integer that is not a multiple of 3. Other phase-shifts and other numbers of similar intensity-modulating elements may also be used as long as the phase-shifts between the projected fringes sets are compatible with phase-shift analysis.

Referring back to the configuration shown in FIG. 4, the structured-light pattern projected when one similar intensity-modulating element is positioned at the proximal end of coherent fiber bundle 71 has a spatial offset or phase-shift of approximately ⅓ of the projected line period, relative to the structured-light pattern projected when a vertical neighboring similar intensity-modulating element is positioned at the proximal end of coherent fiber bundle 71 corresponding to a phase-shift of 120°.

Referring back to FIGS. 2 and 3, patterned zone 120 is vertically movable in the y direction, or generally, in the direction A mentioned above, with step movement such that each step movement positions one similar intensity-modulating element at the proximal end of coherent fiber bundle 71. At least one translation element 130 such as a motor, piezo translator, or solenoid may be used to position the plurality of similar intensity-modulating elements at the proximal end of coherent fiber bundle 71.

For example, the structured-light pattern projected when light passes through similar intensity modulating element 122 has a phase-shift of approximately 120° relative to the structured-light pattern project when light passes through both similar intensity-modulating elements 121 and 123. FIG. 3 shows an exemplary configuration when similar intensity modulating element 122 is positioned at the proximal end of coherent fiber bundle 71. Referring back to FIG. 4, exemplary height h dimensions for each similar intensity-modulating element 121, 122, 123 used with a 100 μm grating period may range from 2 mm-5 mm.

In an alternative embodiment, the at least one patterned zone 120 comprises a patterned zone with a single intensity-modulating element having a repeating pattern, wherein the patterned zone 120 is linearly moveable to a plurality of positions. Pattern selector 70 comprises a precision motion element (not shown) that linearly moves the at least one patterned zone 120 to the plurality of positions. At each position, the light from light source 23 or source fiber bundle 24 is passed through the patterned zone to project a structured-light pattern onto the surface. The positions are chosen such that the structured-light pattern projected when the at least one patterned zone 120 is in one position exhibits a phase-shift relative to the structured-light patterns projected when the at least one patterned zone 120 is in the other positions and wherein the phase-shift is compatible with phase-shift analysis. In one embodiment, the repeating pattern is a line pattern having a period, and each of the plurality of positions is offset from the other positions by n/3 times the period in the direction perpendicular to the lines of the line pattern, where n is an integer that is not a multiple of 3. This offset results in projected structured-light patterns that exhibit a 120° phase-shift relative to one another, which is compatible with phase-shift analysis.

Figure 5:
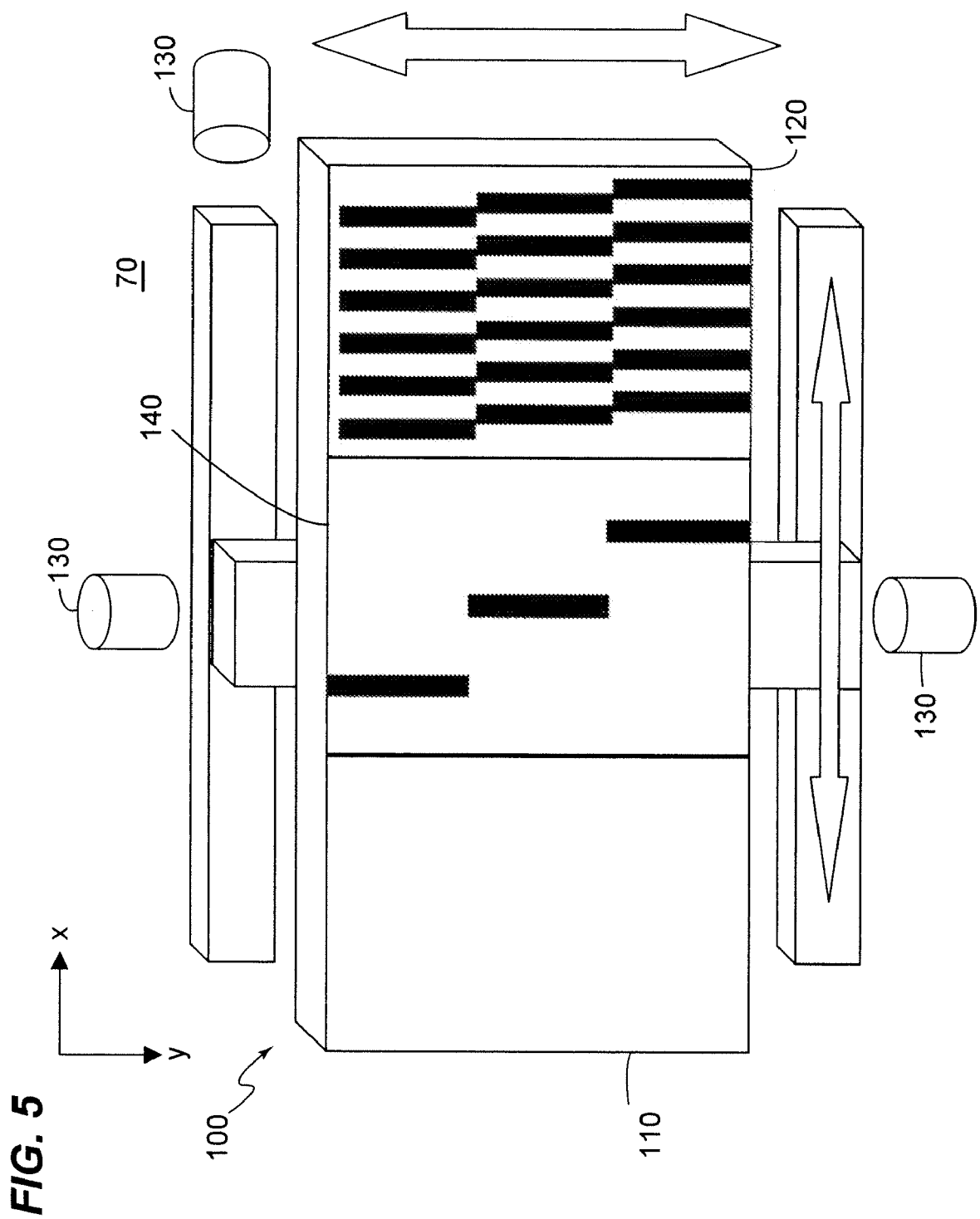
FIG. 5 is a perspective view of an exemplary pattern selector comprising an optically-transmissive element including at least one calibrating zone.

To assist in finding absolute object distance z using phase-shift analysis, probe system 10 projects a calibrating light pattern onto the surface or object. As mentioned above, an additional zone may be included on optically-transmissive element 100 for generating a calibrating light pattern. An exemplary embodiment of pattern selector 70 is shown in FIG. 5 where pattern selector 70 comprises at least one calibrating zone 140. In FIG. 5, calibrating zone 140 is disposed in between clear zone 110 and patterned zone 120, but these zones can be displaced on element 100 in any order. Furthermore, optically-transmissive element 100 is horizontally moveable between zones in order to position the at least one clear zone 110, the at least one patterned zone 120, or the at least one calibrating zone 140 at the proximal end of coherent fiber bundle 71. Alternative embodiments including at least one calibrating zone 140 can be appreciated in view of the description relating to FIG. 2. Furthermore, element 100 including calibrating zone 140 can also be appreciated as it relates to FIG. 3 and its description above.

When calibrating zone 140 is disposed between light source 23 and the proximal end of coherent fiber bundle 71, light from light source 23 passes through calibrating zone 140 to project a plurality of calibrating light patterns on the surface or object. In an embodiment of the invention, the at least one calibrating light pattern comprises a plurality of individual lines that are projected at different angles relative to the field of view. For example, one line might exit the probe at 20° left, one straight, and one 20° right. This way, if the viewed object is, for example, a turbine blade that only covers the right ⅓ of the field of view, at least one of the calibrating lines would still be imaged on the blade. Furthermore, if there is a discontinuity, like a step, on the surface, one calibrating line would likely still be imaged on each of the two surfaces. The calibrating zone 140 shown in FIG. 2 is one example of a calibrating zone for projecting a calibrating light pattern. In addition, the at least one calibrating zone 140 may include, but is not limited to, angled lines, a single line, a plurality of lines, a dot, a plurality of dots, and a plurality of parallel light and dark lines.

In an alternative embodiment, light from the at least one light emitter module 37 projects at least one calibrating or reference light pattern onto the surface or object. In addition, light from the at least one light emitter module 37 may be passed through at least one intensity modulating element 38 to alter the distribution of light and project at least one calibrating light pattern onto the surface. In this case, the origin of the at least one calibrating light pattern differs from the point of origin of the at least one fringe set. Mentioned above, the at least one calibrating light pattern may include, but is not limited to, angled lines, a single line, a plurality of lines, a dot, a plurality of dots, and a plurality of parallel light and dark lines.

The construction and arrangement of the fringe projection system and method for a probe using a coherent fiber bundle, as described herein and shown in the appended figures, is illustrative only. Although only a few embodiments of the invention have been described in detail in this disclosure, those skilled in the art who review this disclosure will readily appreciate that many modifications are possible (e.g. variations in sizes, dimensions, structures, shapes and proportions of the various elements, values of parameters, mounting arrangements, use of materials, orientations, etc.) without materially departing from the novel teachings and advantages of the subject matter recited in the appended claims. Accordingly, all such modifications are intended to be included within the scope of the present invention as defined in the appended claims. The order or sequence of any process or method steps may be varied or re-sequenced according to alternative embodiments. In the claims, any means-plus-function clause is intended to cover the structures described herein as performing the recited function and not only structural equivalents but also equivalent structures. Other substitutions, modifications, changes and omissions may be made in the design, operating conditions and arrangement of the preferred and other exemplary embodiments without departing from the spirit of the embodiments of the invention as expressed in the appended claims. Therefore, the technical scope of the present invention encompasses not only those embodiments described above, but also those that fall within the scope of the appended claims.

What is claimed is:

1. A probe comprising:
   a light source;
   a coherent fiber bundle;
   a pattern selector disposed between the light source and the proximal end of the coherent fiber bundle comprising at least one patterned zone through which light from the light source passes to project at least one fringe set onto a surface, each of the at least one fringe sets comprising a structured-light pattern;
   an imager for obtaining at least one image of the surface; and
   a processing unit that is configured to perform phase-shift analysis on the at least one image.

2. The probe of claim 1, wherein the at least one structured-light pattern comprises parallel light and dark lines and wherein the parallel light and dark lines comprise sinusoidal intensity profiles.

3. The probe of claim 1, further comprising:
   viewing optics which guide and focus light from the surface onto the imager; and
   pattern imaging optics disposed at the distal end of the coherent fiber bundle to image the at least one fringe set onto the surface.

4. The probe of claim 3, wherein the pattern imaging optics comprise a gradient index lens.

5. The probe of claim 3, further comprising:
   a detachable distal tip comprising at least one lens of the viewing optics and the pattern imaging optics.

6. The probe of claim 1, further comprising at least one clear zone.

7. The probe of claim 6, wherein an optically-transmissive element of the pattern selector comprises the at least one clear zone and the at least one patterned zone, wherein the optically-transmissive element is translated between the zones in order to position either the at least one clear zone or the at least one patterned zone at the proximal end of the coherent fiber bundle.

8. The probe of claim 1, further comprising:
   a source fiber bundle disposed between the light source and the pattern selector.

9. The probe of claim 1, wherein the at least one patterned zone comprises a single intensity-modulating element having a repeating pattern.

10. The probe of claim 9, wherein the patterned zone is linearly moveable to a plurality of positions such that the structured-light pattern projected when the at least one patterned zone is in one position exhibits a phase-shift relative to the structured-light patterns projected when the at least one patterned zone is in the other positions.

11. The probe of claim 10, wherein
    the repeating pattern is a line pattern having a period; and each of the plurality of positions is offset from the other positions by n/3 times the period in the direction perpendicular to the lines of the line pattern, where n is an integer that is not a multiple of 3.

12. The probe of claim 1, wherein:
the at least one patterned zone comprises a plurality of similar intensity-modulating elements such that when light passes through each of the plurality of similar intensity-modulating elements a fringe set is projected onto the surface; and
wherein the plurality of similar intensity-modulating elements are positioned such that the structured-light pattern of one fringe set exhibits a phase-shift relative to the structured-light patterns of other fringe sets.

13. The probe of claim 12, wherein the plurality of similar intensity-modulating elements comprise a line grating having a grating period.

14. The probe of claim 12, wherein the plurality of similar intensity-modulating elements are positioned such that the structured-light pattern of one fringe set exhibits a phase-shift of 120° relative to the structured-light pattern of adjacent fringe sets.

15. The probe of claim 12, wherein the plurality of similar intensity-modulating elements comprise a repeating pattern with a period and are stacked in a direction A such that one of the plurality of similar intensity-modulating elements is displaced from an adjacent similar intensity-modulating element by n/3 times the period in the direction perpendicular to direction A, where n is an integer that is not a multiple of 3.

16. The probe of claim 15, further comprising:
at least one translation element used to position the plurality of similar intensity modulating elements at the proximal end of the coherent fiber bundle, wherein the at least one patterned zone is movable in the direction A with step movement such that each step movement positions one of the plurality of similar intensity-modulating elements at the proximal end of the coherent fiber bundle.

17. The probe of claim 1, further comprising a calibrating zone through which light is passed to project at least one calibrating light pattern onto the surface.

18. The probe of claim 1, wherein the pattern selector comprises at least one calibrating zone.

19. The probe of claim 17, wherein the at least one calibrating light pattern comprises a plurality of lines.

20. A method for projecting a plurality of fringe sets suitable for phase-shift analysis on a surface using a probe, comprising:
disposing a pattern selector between a light source and the proximal end of a coherent fiber bundle, the pattern selector comprising at least one patterned zone;
passing light from the light source through the coherent fiber bundle and the at least one patterned zone to project structured-light patterns onto the surface such that the structured-light patterns projected exhibit a phase-shift relative to one another, the phase-shift being compatible with phase-shift analysis.

* * * * *